United States Patent [19]

Green

[11] 4,309,418

[45] Jan. 5, 1982

[54] ANTI-TUMOR AGENT FROM HUMAN SERUM AND PROCESS

[75] Inventor: Saul Green, New York, N.Y.

[73] Assignee: Sloan-Kettering Research Institute for Cancer, New York, N.Y.

[21] Appl. No.: 133,742

[22] Filed: Mar. 25, 1980

[51] Int. Cl.$^3$ .................... A61K 37/00; A61K 35/14; A23J 11/06; C07G 7/00

[52] U.S. Cl. .............................. 424/177; 260/112 R; 424/101

[58] Field of Search ............................. 424/101, 177; 260/112 R

[56] References Cited

U.S. PATENT DOCUMENTS

| | | | |
|---|---|---|---|
| 2,876,168 | 3/1959 | Brogg et al. | 424/57 |
| 3,105,013 | 9/1963 | Saul et al. | 424/52 |
| 3,105,798 | 10/1963 | Holliday et al. | 424/52 |
| 3,151,027 | 9/1964 | Cooley et al. | 424/52 |
| 3,257,282 | 6/1966 | Muhler et al. | 424/52 |
| 3,282,792 | 11/1966 | Fiscella | 424/52 |
| 3,330,732 | 7/1967 | Muhler | 424/49 |
| 3,337,412 | 8/1967 | Elbreder | 424/151 |
| 3,378,445 | 4/1968 | Muhler | 424/49 |
| 3,445,567 | 5/1969 | Muhler | 424/52 |
| 3,756,386 | 9/1973 | Marckhardt | 206/47 A |
| 3,804,946 | 4/1974 | Harrison et al. | 424/54 |
| 4,009,257 | 2/1977 | Thomas et al. | 424/101 |
| 4,016,255 | 4/1977 | Forward et al. | 424/52 |
| 4,076,701 | 2/1978 | Burton et al. | 424/101 |

FOREIGN PATENT DOCUMENTS 845611  8/1960  United Kingdom.

OTHER PUBLICATIONS

Applicant's Translation of George et al. East Germany Offen. 28 16 513 Oct. 28, 1978, "Process for Manufacture of a Solid Tooth Care Agent" (Veb Elbe-Chemie, D.D.R.)(Tablet or Powder, Which Forms Paste, Upon Wetting, Eliminating Glycerin, Wherein Moisture-Sensitive Ingredients Such as Enzymes, Vitamins, etc. (0.01-1%) are Mixed with 35-40% Cleaning Agent, Preferably 37% $CrHPC_4$, $2H_2O$; $CA_2P_2O_7$ and/or Al$(OH)_3$, 55-60%, Microcrystalline cellulose, 1-3% Frothing Agent, 1-1.5% Aroma, 0.15% Saccharin 1-3% Binder, Preferably Guar Flour, CMC, Algae Ext., and Processed into Tablets.)

*Primary Examiner*—Sam Rosen
*Attorney, Agent, or Firm*—Sprung, Felfe, Horn, Lynch & Kramer

[57] ABSTRACT

The invention relates to an anti-tumor agent prepared from human serum by the process steps of multiple salting out, centrifuging, desalting and gel filtration.

14 Claims, No Drawings

ANTI-TUMOR AGENT FROM HUMAN SERUM AND PROCESS

The invention described herein was made in the course of work under a grant or award from the Department of Health, Education and Welfare.

BACKGROUND

This invention relates to an anti-cancer agent and process for preparing same. More particularly, this invention relates to an agent obtained from human serum which inhibits and/or prevents the growth of tumor cells.

The presence of an anti-tumor factor (TNF, tumor necrosis factor) in the serum of animals has been described in Cancer Letters, 6: 235–240 (1979).

Following the injection of bacterial endotoxin, TNF is found in the serum of mice inoculated with *Corynebacterium parvum* (CP). TNF was purified about 50 fold and is believed to be a $\alpha_2$ globulin having a molecular weight of about 150,000. TNF was detected by an in vitro assay using mouse L-cells and by an in vivo bioassay, using female BALB/c mice bearing a methyl cholanthrene-induced fibrosarcoma.

TNF-like activity has been found in extracts of liver microsomes from CP-treated mice and in very low, but measurable amounts in microsomes from livers of normal mice. TNF has also been found in the serum of normal mice.

A fraction of the $\alpha_1$- $\alpha_2$ globulins from serum of normal humans has been found to be cytotoxic for mouse L cells in culture and Meth A tumors in mice (Cancer Letters, 6: 235–240 1979) and inhibited the growth, in vitro, of human colon cancer, melanoma and neuroblastoma cells lines (J. Cell. Biol., 79: 67, 1978).

SUMMARY

The present invention provides a process for preparing an anti-tumor agent from human serum. Blood is coagulated naturally and the serum is separated from the coagulated components. The serum is centrifuged to remove fats. The serum is diluted with an isotonic buffer and a first portion of proteins is removed by salting out, for example from a 35% saturated solution of ammonium sulfate. A second portion of proteins is recovered from the same serum by further salting out, for example from a 70% saturated solution of ammonium sulfate. The second portion of proteins is collected, dialyzed to remove the salt and gel filtered. A gel filtered active fraction having a molecular weight of more than 150,000 is collected.

DESCRIPTION

The blood employed in the process of the present invention is human blood and all steps should be carried out under sterile conditions. The blood is allowed to coagulate naturally and the coagulated components are removed from the blood serum by centrifugation.

The isotonic buffer employed in diluting the serum is preferably an aqueous solution of about 0.05 molar in potassium phosphate and containing about 0.9 percent of sodium chloride. The dilution can be achieved by admixing about one-half to two-fold volume of isotonic buffer solution with the serum.

Dialysis is preferably carried out using a semi-permeable casein membrane having a pore size for excluding molecules having a molecular weight of more than 10,000.

The recovered protein portion is preferably gel filtered through a polyacrylamide-dextran gel. The gel filtered protein is separated into fractions depending on the running time through the filter. The active fraction (called "nHG") is further separated by electrophoresis on a semi-solid gel comprising acrylamide and a cross-linking.

The present invention further provides an anti-tumor agent from human serum comprising a protein fraction (nHG) having a molecular weight of more than about 150,000 which is stable to heat at 90° C. for at least one hour, non-dialyzable and inhibits the growth of HeLa tumor cells in vitro. The nHG fraction can be dispersed in an aqueous solution to a final concentration from 0.5 to 2.5% and is preferably dispersed in an isotonic saline solution. The nHG fraction can be further concentrated by freeze drying.

The blood is allowed to clot naturally and the coagulated material is separated by centrifuging. The serum is then further processed in an ultra centrifuge. The centrifugal force can range from about 10,000 g to about 200,000 g and is preferably about 105,000 g. The centrifuging time can range from about 2 minutes to 2 hours. Preferred centrifuging time is 15 minutes.

The remaining serum is diluted with a buffer which contains a salt or salts from the group of potassium phosphate and sodium chloride. The concentration of the buffer solution is preferably about 0.05 molar in phosphate and about 0.9% sodium chloride. A 0.9% concentration of sodium chloride provides an isotonic solution. The serum is diluted with about from ½ to 2 times the volume of the serum with the buffer solution. Preferably the amount of buffer added to the serum is of the same volume.

The following steps are carried out at 4° C. using a water and ice mixture.

One hundred ml of the buffered serum solution are taken and under stirring anhydrous ammonium sulfate is added slowly. The amount of anhydrous ammonium sulfate is 24.5 g which brings the solution to about 35% saturation. During the addition of the ammonium sulfate, ammonium hydroxide is added at the same time to counteract the acidity of the ammonium sulfate and to keep the pH value constant at 7. The addition of the ammonium sulfate causes a first portion of proteins to precipitate. This solution is allowed to stand at 4° C. for one hour. The serum is now centrifuged under conditions similar to those of the prior centrifugation step, e.g. at a force of 105,000 g for about 15 minutes. The resulting precipitate is discarded and another 24.5 g of ammonium sulfate is added to the solution in the manner described above along with ammonium hydroxide to keep the pH value at about 7. The solution is allowed to stand for about 1 hour at 4° C. and is centrifuged again. At this point the serum is discarded and the precipitate is collected.

The precipitate is dialyzed to remove the salt in a commercially available membrane made from semi-permeable casein. The pores of the membrane exclude passage of materials having a molecular weight of more than about 10,000 and preferably 20,000 and above. The dialyzing medium is an isotanic aqueous solution containing 0.9% sodium chloride.

The solution resulting from the dialyzing process is then subjected to gel filtration. The gel employed can be Sephacryl S-200 which contains beads having a diameter of about 40–105 μm which are swelled with water and consists of polyacrylamide plus dextran. Every 100 drops of the filtrate are collected separately and if desired, concentrated by lyophilization (freeze drying). After the lyophilization the resulting concentrate is dialyzed to remove the salt. The resulting fractions are then contacted with tumor cells such as HeLa cells which have originally been obtained from humans having cervical cancer. The cells (500) are placed in a Petri dish. Then the cells are contacted with a fraction obtained by the process described. Thereafter, nutrient solution medium is added to allow the cells to grow. In a control or blank test where no nHG is added, numerous cells grow and can be stained with a dye such as Amido Black.

The initial fraction of the gel filtration containing the highest molecular weight proteins is the most active agent. The molecular weight of this material is at least 150,000 and is believed to be derived from an $\alpha$-globulin of the human serum. The active fraction remains stable to heat at 90° C. for at least one hour. The nHG fraction can be subjected to dialysis with a Visking membrane excluding the passage of molecules having a molecular weight of higher than about 20,000. The agent remains active.

The active fraction was further analyzed by electrophoresis on a semi-solid gel comprising acrylamide and a cross-linking agent. The resulting fractions of proteins in the gel were stained with Coomassie Blue G-250. For each gel in the analysis about 4 mg of substance can be employed. The speed of passage through the gel depends on the size and the charge of the molecules. Albumin moves relatively fast having a molecular weight of only about 70,000 and appears at the bottom of the gel. A pattern evolved showing at the top about 4 rings of stained proteins which indicated the various components of the active composition. The active nGH fraction can be extracted from slices of the gel.

The active nHG fraction can be further analyzed by immunoelectrophoresis. In the immunoelectrophoresis it is found that the nHG fraction included albumin, haptoglobulin (an agent active against inflammation), $\alpha_1$-anti-trypsin and an $\alpha_2$-macroglobulin.

The immunoelectrophoresis also indicates that the active nHG fraction does not contain immunoglobulin, IGG, IGA, IGM and Kappa chains and Lambda chains.

EXAMPLE

Preparation of active nHG fraction from serum. All procedures were carried out at 4° C. One hundred milliliters of serum was sterilized by filtration through a sterile 0.22 μm millipore filter and was diluted with 100 ml of sterile phosphate-buffered saline (PBS). Forty-nine grams of solid $(NH_4)_2SO_4$ was added slowly with stirring. The pH was maintained at 7.0 by addition of $NH_4OH$. The precipitated protein was removed by centrifugation at 105,000×g for 15 minutes and 49 g of $(NH_4)_2SO_4$ was added to the supernatant solution with stirring. The insoluble material [35–70% saturation with respect to $(NH_4)_2SO_4$] was collected by centrifugation, taken up in a small volume of sterile water, dialyzed against sterile PBS containing penicillin and streptomycin from the Sloan-Kettering Institution Media Laboratory until free of $(NH_4)_2SO_4$ and diluted with sterile PBS to a final protein of 500–700 mg/ml.

Gel filtration of the 35–70% fraction was carried out on a column of Sephacryl S-200 (superfine), from Pharmacia, Upsala, Sweden, previously equilibrated against Sterile PBS. The bed height was 85 cm., the eluant was PBS and the flow rate was 15 ml/h. The gel column was first calibrated for determination of molecular weights with dextran blue (void volume), purified aldolase (160,000), bovine serum albumin (67,000), soybean trypsin inhibitor (21,600), and cytochrome c (12,500). Ten milliliters aliquots of the dialyzed 35–70% fraction from each test serum were filtered through the column and the protein which was eluted between 195 and 236 ml of PBS was pooled, concentrated by lyophilization and dialyzed against 0.15 M NaCl until free of phosphate. The concentrated material, called nHG, was sterilized by filtration through a sterile Nalgene 0.22 μm filter.

Protein was determined by the method of Lowry et al. (1951): Protein measurement with the Folin phenol reagent, J. Biol. Chem., 193: 265–275, agarose electrophoresis was as described in the Corning Operations Manual for Agarose Electrophoretic Systems No. 47166, Corning 490; San Antonio Road, Palo Alto, Calif.

A purified fraction (nHG) of the $\alpha_1$–$\alpha_2$ globulins was prepared from serum by ammonium sulphate fractionation, Sephadex filtration, PAG-electrophoresis and affinity chromatography. Its effect on two normal fibroblast cell lines (W138) and one from human skin, maintained at (MSKCC) and on HeLa cells were determined. Survival of the HeLa cells is disclosed in terms of colony formation by single cells, following a 24-hour exposure to 50, 100, 150, 200 or 250 μg nHG/ml. At these doses, cell survival relative to controls was 90%, 78%, 16%, 3% and 0.5%, respectively. In contrast, W138 and skin fibroblast cells grew normally after 24 hours of exposure to 500 μg nHG/ml. Whole human serum, buffer extracts of the Sephadex column and non-globulin proteins had no anti-NeLa cells activity. Dialysis of nHG in the presence and absence of EDTA did not alter its activity. Up to 100 μg E. coli endotoxin/ml did not inhibit HeLa cell growth. These effects were recorded by time lapse cinematography. Five hundred μg nHG/ml was seen to be first cytostatic then cytotoxic; 50% of the HeLa cells were dead after 41 hours and more than 95% were dead in 44 hours. Under identical conditions no adverse effects were seen in the normal fibroblast cell cultures in 60 hours.

What is claimed is:

1. Process for preparing an anti-tumor agent from buffered human serum which comprises:
   (i) removing a first portion of proteins from the serum by addition of ammonium sulfate salt in an amount up to about 35% of the amount necessary to form a saturated solution while maintaining the pH at 7; thereafter
   (ii) centrifuging the serum at a force of 105,000 g to separate the first portion of proteins, and discarding the first portion of proteins;
   (iii) recovering a second portion of proteins from the serum by addition of ammonium sulfate salt in an amount to total an amount greater than about 35% up to about 70% of the amount necessary to form a saturated solution while maintaining the pH at 7, and retaining the second portion of proteins;
   (iv) desalting the second portion of proteins;
   (v) gel filtering the desalted proteins; and
   (vi) collecting a gel filtered active fraction having a molecular weight greater than 150,000.

2. Process of claim 1 wherein fats are removed before salting out the first portion of proteins.

3. Process of claim 1 carried out under sterile conditions.

4. Process of claim 1 wherein an isotonic buffer is added to the serum before salting out the first portion of proteins.

5. Process of claim 4 wherein the isotonic buffer is an aqueous solution of about 0.05 molar potassium phosphate containing about 0.9 percent of sodium chloride.

6. Process of claim 1 wherein dialysis is carried out with a membrane having a pore size which excludes molecules having a molecular weight of more than about 10,000.

7. Process of claim 1 wherein the filtering gel is a polyacrylamide dextran gel.

8. Process of claim 1 further comprising separating and extracting the active fraction on a semisolid gel.

9. The process of claim 1 wherein said first portion of proteins is removed by an addition of sufficient salt to form an approximately 35% saturated solution; and said second portion of proteins is recovered by an addition of sufficient salt to form an approximately 70% saturated solution; thereby to optimize the recovery of said agent.

10. Anti-tumor agent derived from human serum comprising a protein fraction having a molecular weight of more than 150,000 which is stable at 90° C. for at least one hour, non-dialyzable and inhibits the growth of HeLa tumor cells.

11. Anti-tumor agent of claim 10 in an aqueous solution having a concentration of said agent of from about 0.1 to about 2.5 percent.

12. Anti-tumor agent of claim 11 in an isotonic aqueous solution.

13. Anti-tumor agent of claim 10 lyophilized.

14. Process inhibiting the growth of tumor cells comprising contacting the tumor cell lines in vitro with the product of claim 10.

* * * * *